US008788522B2

(12) United States Patent
Kimura

(10) Patent No.: US 8,788,522 B2
(45) Date of Patent: Jul. 22, 2014

(54) PAIR CHARACTER STRING RETRIEVAL SYSTEM

(75) Inventor: Kouichi Kimura, Koganei (JP)

(73) Assignee: Hitachi, Ltd., Tokyo (JP)

( * ) Notice: Subject to any disclaimer, the term of this patent is extended or adjusted under 35 U.S.C. 154(b) by 463 days.

(21) Appl. No.: 13/264,037

(22) PCT Filed: Apr. 5, 2010

(86) PCT No.: PCT/JP2010/056146
§ 371 (c)(1),
(2), (4) Date: Oct. 12, 2011

(87) PCT Pub. No.: WO2010/119783
PCT Pub. Date: Oct. 21, 2010

(65) Prior Publication Data
US 2012/0041977 A1  Feb. 16, 2012

(30) Foreign Application Priority Data
Apr. 13, 2009  (JP) ................. 2009-097270

(51) Int. Cl.
*G06F 7/00* (2006.01)
*G06F 19/22* (2011.01)
*G06F 17/30* (2006.01)

(52) U.S. Cl.
CPC .......... *G06F 17/30985* (2013.01); *G06F 19/22* (2013.01)
USPC ....................................... 707/770

(58) Field of Classification Search
CPC ............... G06F 17/30545; G06F 17/30864; G06F 17/30; G06F 17/30283; G06F 17/30424; G06F 17/3087; G06F 17/30477; G06F 17/30241

USPC .................................... 707/752, 770
See application file for complete search history.

(56) References Cited

FOREIGN PATENT DOCUMENTS

| JP | 2000-259646 A | 9/2000 |
| JP | 2001-243238 A | 9/2001 |

OTHER PUBLICATIONS

Service RF. Gene Sequencing, The race for the $1000 Genome, Science, Mar. 17, 2006, 311 (5767); 1544-6.
U. Manber et al., Suffix Arrays: A New Method for On-Line String Searches, 1st ACM-SIAM, Symposium on Discrete Algorithms, pp. 331-327, 1990.
J. Korbel et al., Paired-End Mapping Reveals Extensive Structural Variation in the Human Genome, Science, Oct. 19, 2007, pp. 420-426.

(Continued)

*Primary Examiner* — Truong Vo
(74) *Attorney, Agent, or Firm* — Mattingly & Malur, PC

(57) ABSTRACT

A data structure of index information for retrieving pair character strings on a computer at high speed is provided. A method of retrieving a pair character strings appearing in close proximity of each other in a document using the index information at high speed is also provided. Bits of a suffix array of reference document data are rearranged, thereby creating index information LSA localizable, or usable as an index for a subregion of the document. Through use of this, a process of dichotomizing a region, where the entire document is designated as an initial region, is repeated and positions of index information for a query character string in the reference document data are gradually detailed. The distance between the pair is evaluated and candidates are narrowed down. Finally, positions where the pair character strings occur in close proximity of each other are identified.

6 Claims, 14 Drawing Sheets

(56) References Cited

OTHER PUBLICATIONS

R. Lippert, Space-Efficient Whole Genome Comparisons with Burrows-Wheeler Transforms, Journal of Computational Biology, 12(4), pp. 407-415, 2005.

R. Gonzalez et al., Practical Impletmentation of Rank and Select Quiries, in Proc. WEA'05, pp. 27-38, 2005.

H. Li et al., Mapping short DNA sequencing reads and calling variants using mapping quality scores, Genome Res. 2008 18, pp. 1851-1858.

K. Kimura et al., Localized Suffix Array and Its Application to Genome Mapping Problems for Paired-End Short Reads, Genome Informatics 2009, Dec. 16, 2009, Genome Informatics Series vol. 23, pp. 60-71.

K. Kimura, Cho Heiretsu DNA Sequencer Muke Kosoku-Koseido Genome Mapping Shuho, Shoroku CD Seikagaku, Dec. 4, 2008, 4T9-3.

Fig. 8

801
0 "abracad"
1 "bracad"
2 "rcad"
3 "acad"
4 "cad"
5 "ad"
6 "d"
7 ""

802
7 ""
0 "abracad"
3 "acad"
5 "ad"
1 "bracad"
4 "cad"
6 "d"
2 "rcad"

803
7 = 1 1 1
0 = 0 0 0
3 = 0 1 1
5 = 1 0 1
1 = 0 0 1
4 = 1 0 0
6 = 1 1 0
2 = 0 1 0

804
1 0 0 1 0 1 1 0
0 1 0 1 1 0 0 1
0 1 1 0 1 0 1 0

PAIR CHARACTER STRING RETRIEVAL SYSTEM

TECHNICAL FIELD

The present invention relates to a method for retrieving two character strings appearing in close proximity to each other at high speed from large-scale genome sequence data or massive general document data using a computer. In particular, the present invention relates to a method for high-speed identification of positions on a genome that correspond to massive DNA sequence data acquired from a massively parallel DNA sequencer using a paired-end method.

BACKGROUND ART

In recent years, a massively parallel DNA sequencer based on a new principle completely different from that of a conventional capillary DNA sequencer has appeared (Non Patent Literature 1). The massively parallel DNA sequencer can read a lot, or tens of millions, of sequences at one time. However, there is a disadvantage in that the read sequence length is tens of nucleotides, which is relatively short. Thus, in order to compensate the disadvantage, a paired-end method is employed (Non Patent Literature 3). The paired-end method sequences tens of nucleotides from both ends of a multiplicity of genome sequence fragments approximately controlled to a certain length (from hundreds of nucleotides to thousands of nucleotides), thereby allowing information of pairs of nucleotide sequences (paired-end sequences) about a certain interval apart from each other on genomes to be acquired.

A genome mapping computation is performed on paired-end sequence data, acquired by a sequencer analyzing a genome DNA sample, with respect to a reference genome sequence. That is, a computation is made to determine at which positions the sequence acquired by sequencing appear on the reference genome sequence, and it is checked whether a distance of an expected separation between mapping positions of paired sequences on the reference genome is kept or not. This allows structural variations, such as insertions and deletions between the sample genome and the reference genome, to be detected. That is, if the distance between the mapping positions is larger than the expected separation, it is considered that deletions have occurred between the pair of sequences on a sample genome side. In contrast, if the distance between the mapping positions is smaller than the expected separation, it is considered that insertions have occurred between the pair of sequences on the sample genome side (Non Patent Literature 3).

If the sequence length is short, there may be a case where the mapping positions are not uniquely determined in the genome mapping computation and a lot of positions are listed as candidates. It can be expected that, even in such a case, use of the mapping position separation of the paired sequences as a constraint, that is, use of the constraint that the mapping positions are in close proximity to each other, uniquely determines the mapping positions as the pair sequences or narrows down the candidates to a small number of candidates. As to paired-end sequence data acquired by the sequencer analyzing a transcription product sample, there may be a case where an intron is intervened between the mapping positions of the paired sequences and the separation between the mapping positions may become longer by the intron length. Even in this case, the constraint that the separation between the mapping positions does not exceed the length of gene region on the genome can be used for mapping computation as paired sequences.

In a case of performing genome mapping computation of massive sequence data (query sequence data) on a large-scale reference genome sequence, typically reference genome sequence data is preliminarily indexed. Use of the index can speed up retrieval of the query sequence. A suffix array (Non Patent Literature 2) can be employed as an indexing method.

MAQ has been known as software capable of mapping massive paired sequences data of the massively parallel DNA sequencer analyzed by the paired-end method, on the reference genome sequence at high speed and with high accuracy (Non Patent Literature 6). MAQ preliminarily creates index information of massive paired sequences data, and retrieves candidates of mapping positions while scanning the reference genome sequence and referring to index information. In order to consider a condition that paired sequences are mapped in close proximity to each other while satisfying a distance constraint, up to the last two candidates of positions to be mapped on the plus strand of a genome sequence per query sequence are held in storing region of a computer in a scanning process and at the same time, candidates of positions to be mapped on the minus strand are retrieved, and it is determined whether a pair with mapping positions on the plus strand that hold the found mapping positions on the minus strand and satisfying the constraint on distance can be created or not. This efficiently evaluates combinations of candidates of mapping positions of the paired sequences.

CITATION LIST

Non Patent Literature

Non Patent Literature 1: Service RF. "Gene sequencing. The race for the $1000 genome." Science. 2006 Mar. 17; 311 (5767): 1544-6.
Non Patent Literature 2: Manber, U. and Myers, G.: Suffix arrays: A new method for on-line string searches, in 1st ACM-SIAM, Symposium on Discrete Algorithms, pp. 319-327 (1990).
Non Patent Literature 3: Jan O. Korbel, Alexander Eckehart Urban, Jason P. Affourtit, Brian Godwin, Fabian Grubert, Jan Fredrik Simons, Philip M. Kim, Dean Palejev, Nicholas J. Carriero, Lei Du, Bruce E. Taillon, Zhoutao Chen, Andrea Tanzer, A. C. Eugenia Saunders, Jianxiang Chi, Fengtang Yang, Nigel P. Carter, Matthew E. Hurles, Sherman M. Weissman, Timothy T. Harkins, Mark B. Gerstein, Michael Egholm, and Michael Snyder, Paired-End Mapping Reveals Extensive Structural Variation in the Human Genome, Science 19 Oct. 2007: 420-426.
Non Patent Literature 4: Ross Lippert, Space-efficient whole genome comparisons with Burrows-Wheeler transforms, Journal of Computational Biology, 12(4), pp. 407-415, 2005.
Non Patent Literature 5: R. Gonzalez, S. Grabowski, V. Makinen, and G. Navarro. Practical Implementation of Rank and Select Queries. In Proc. WEA'05, pages 27-38, 2005.
Non Patent Literature 6: Heng Li, Jue Ruan and Richard Durbin, Mapping short DNA sequencing reads and calling variants using mapping quality scores. Genome Res. 2008 18: 1851-1858.

SUMMARY OF INVENTION

Technical Problem

In a case of searching paired sequences for mapping positions in close proximity within a designated separation at high speed, it is sufficient that mapping positions on each sequence be independently acquired at high speed using the index and subsequently what satisfies the interval constraint is selected from among combinations of the mapping positions. However, in a case of relatively short sequence length, if the mapping positions of the paired sequences are independently acquired without using the interval constraint, a lot of candidate positions are acquired initially and subsequently a small number of positions satisfying the interval constraint are selected. This may reduce processing speed. On the other hand, in a typical high speed searching method using an index, such as a suffix array, it is difficult to search in consideration of the interval constraint. In MAQ, in a case of a lot of candidates of mapping positions of the paired sequences, oversight may occur according to a certain relative positional relationship.

It is an object of the present invention to acquire at high speed a combination of mapping positions of paired sequences in which the separation between the mapping positions of the pair is within a preliminarily designated value when large-scale reference genome sequence data and massive paired-end sequence data (query sequence data) are provided.

Solution to Problem

Genome sequence data is indexed so as to have information equivalent to a typical suffix array for the entire genome sequence and, also for a subregion of the genome restricted according to various scales, to acquire index information restricted to the subregion (local index information). A method of dividing the index information corresponding to a certain region of the genome into index information for subregions when the index information is dichotomized. As to the paired sequences, initially the entire genome region is searched independently from each sequence to acquire index information, subsequently dichotomy is repeated until the region length becomes one, and thereby genomic positional coordinates for the indices are gradually determined in further detail. In this process, in consideration of distance constraint between the pair, index information that does not satisfy the constraint is removed.

A pair character string retrieval system according to the present invention includes: a storing device storing a reference character string; an input device inputting paired first and second character strings, and an upper limit value of a distance between the first and second character strings; a suffix array construction processor constructing a suffix array of the reference character string; an index range retrieval processor computing an index range in the suffix array for each of the first and second character strings in an independent manner; an LSA construction processor that constructs localizable index information LSA; an index range localization processor; an evaluation processor of the distance between index ranges; and an output device outputting positions on the reference character string of the first and second character strings paired in a distance not exceeding the upper limit value, wherein the index range localization processor removes information of the index range incapable of creating a pair in a distance not exceeding the upper limit value, as a result of information of the index range which becomes null in the computation process and evaluation by the evaluation processor of the distance between index ranges.

The LSA construction processor designates the suffix array of the reference character string as an initial block, divides the suffix array into two blocks corresponding to subregions that are first and second halves of the reference character string according to most significant bits thereof being zero or one, designates arrangement of the most significant bits, having been referred to, as a first column of LSA, further dichotomizes the acquired two blocks according to whether second significant bits are zero or one, thus dividing these two blocks into four blocks corresponding to subregions dividing the entire reference genome sequence into four, designates arrangement of the second significant bits, having been referred to, as a second column of LSA, repeats analogous processing until the length of the subregion becomes one, computes each column of LSA in the processing, and thereby constructs LSA.

The index range localization processor designates the respective index ranges in the suffix array that correspond to the first and second character strings as index ranges in the initial block, divides the index range in the initial block into the index ranges in the blocks using information of the first column of the LSA according to division into the two blocks corresponding to the subregions that are the first and second halves of the reference character string, divides the index ranges in the two blocks into index ranges in the four blocks using information of the second column of the LSA according to division into the four blocks corresponding to the subregions dividing the entire reference character string into four, repeats analogous division processing thereafter, and performs computation of localizing the index range in the initial block into the index range in the subregion in the reference character string. The index range localization processor applies a rank function to the block of each column of the LSA, and computes the positions of the index ranges in the two blocks that are divisions of the block concerned.

The evaluation processor of the distance between index ranges evaluates an upper limit of a distance between the first and second character strings localized into the subregions in the reference character string such that positional coordinates of the index ranges localized into the subregions on the reference character string have a remaining uncertainty range corresponding to the subregions.

Advantageous Effects of Invention

According to the present invention, the index information for the subregion that does not satisfy the distance constraint between the pair is removed in the process of detailing the positional coordinates by division of the region. This allows high speed index search (mapping computation) in consideration of the interval constraint on the mapping positions.

BRIEF DESCRIPTION OF DRAWINGS

FIG. 8 is a diagram illustrating a specific example of constructing LSA.

DESCRIPTION OF EMBODIMENTS

Embodiments of the present invention will hereinafter be described in detail with figures.

Embodiment 1

This embodiment describes a method of acquiring mapping positions in close proximity within a designated separation in a case where a reference genome sequence data and a pair of query sequence is provided. In this embodiment, it is assumed that perfect matching is employed as mapping between the query sequence and the genome sequence. However, this is applicable to imperfect matching that permits mismatch of several nucleotides, by easy analogy. This embodiment considers a constraint only on an upper limit of the separation between mapping positions of the paired sequences. At the same time, a constraint on a lower limit of the separation between mapping positions of the paired sequences can also be considered by easy analogy.

Figure 1:
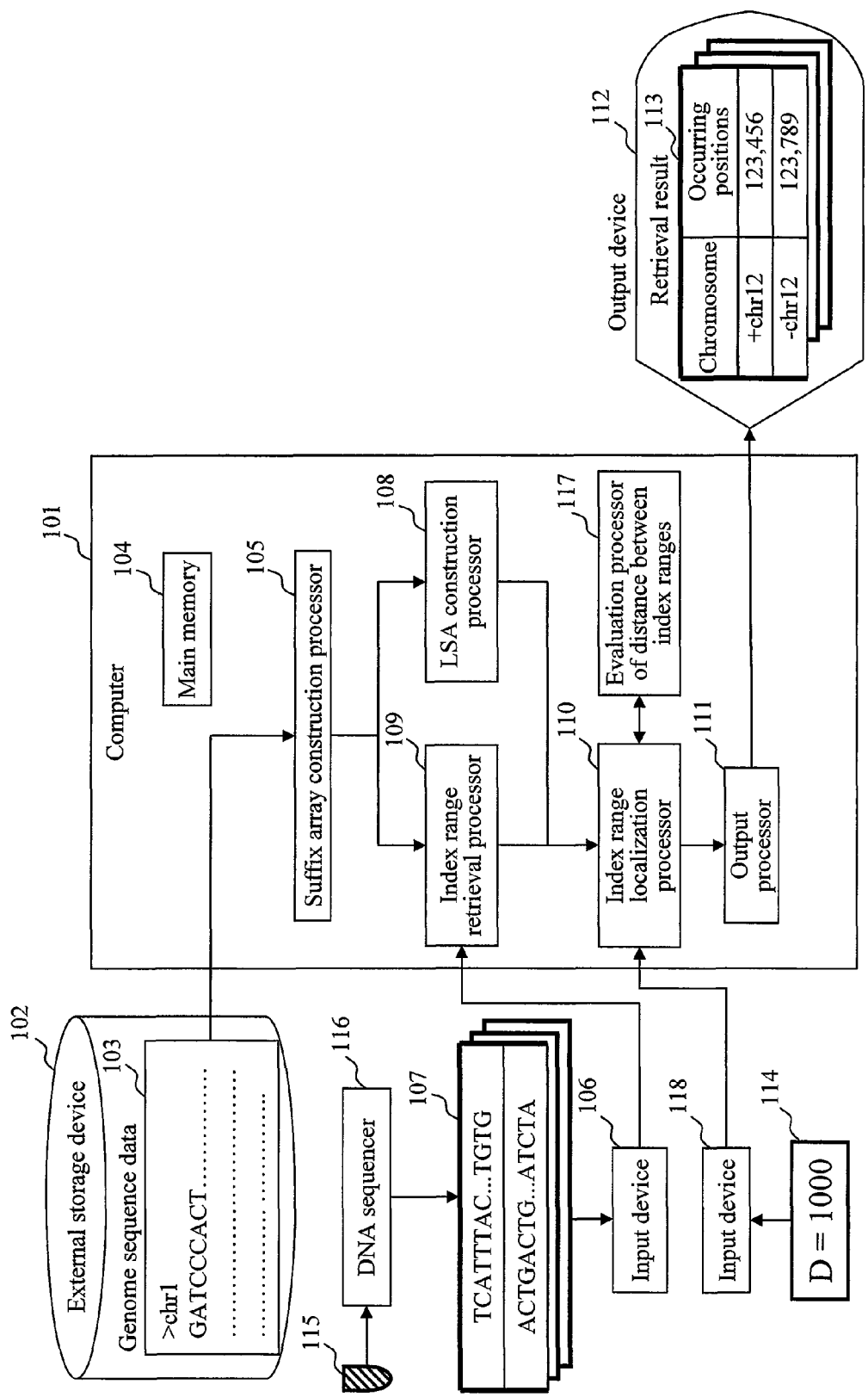
FIG. 1 is a diagram showing an example of a configuration of a system that performs genome mapping computation on paired sequences.

FIG. 1 is a diagram of an example of a configuration of a system that performs mapping computation on paired sequences of this embodiment. Reference numeral 101 denotes a computer operating this system. This computer reads reference genome sequence data 103 stored in an external storage device 102, reads via an input device 106 paired sequences data (a pair of query sequences) 107 acquired by analyzing a DNA sample 115 using a DNA sequencer 116, and reads via an input device 118 a parameter 114 (an upper limit value D of the distance between the pair) designated by a user. The computer 101 causes a suffix array construction processor 105 to connect nucleotide sequences in the reference genome sequence data 103 via a delimiter $, and computes the suffix array thereof and stores the suffix array in a main memory 104. Likewise, computation results of other processors are stored in the main memory 104. The contents of the results are referred to by each processor as necessary. An LSA construction processor 108 constructs an index information LSA (localized suffix array) on the basis of the suffix array. An index range retrieval processor 109 searches the suffix array with respect to each of the paired query sequences in an independent manner, and acquires information of the index range. The index range localization processor 110 localizes (subdivides) the index range satisfying the mapping position interval constraint between the pair based on information of the index range of the query sequence and LSA of the reference genome sequence, and details the genome positions of the index range from a state of spreading over the entire initial genome to a final state of identification in detail to a nucleotide level.

Finally, this allows mapping positions of the paired sequences to be acquired. In order to check success or failure of mapping position interval constraint between the pair, the distance between genome positions of different index ranges are evaluated by an evaluation processor of the distance between index ranges 117. An output processor 111 outputs mapping positional information (retrieval result 113) of paired sequences to an output device 112. The mapping positional information (retrieval result 113) of the paired sequences includes information of chromosome names and directions thereof (which one of + and − strands) and coordinates of occurring positions.

In order to construct the suffix array from the reference genome sequence, a publicly-known method, such as Manber-Myers, may be used (Non Patent Literature 2). In order to acquire index information of a query sequence, that is, an index region where the query sequence appears as a prefix of a suffix in the suffix array, a general dichotomizing search may be used.

Figure 2:
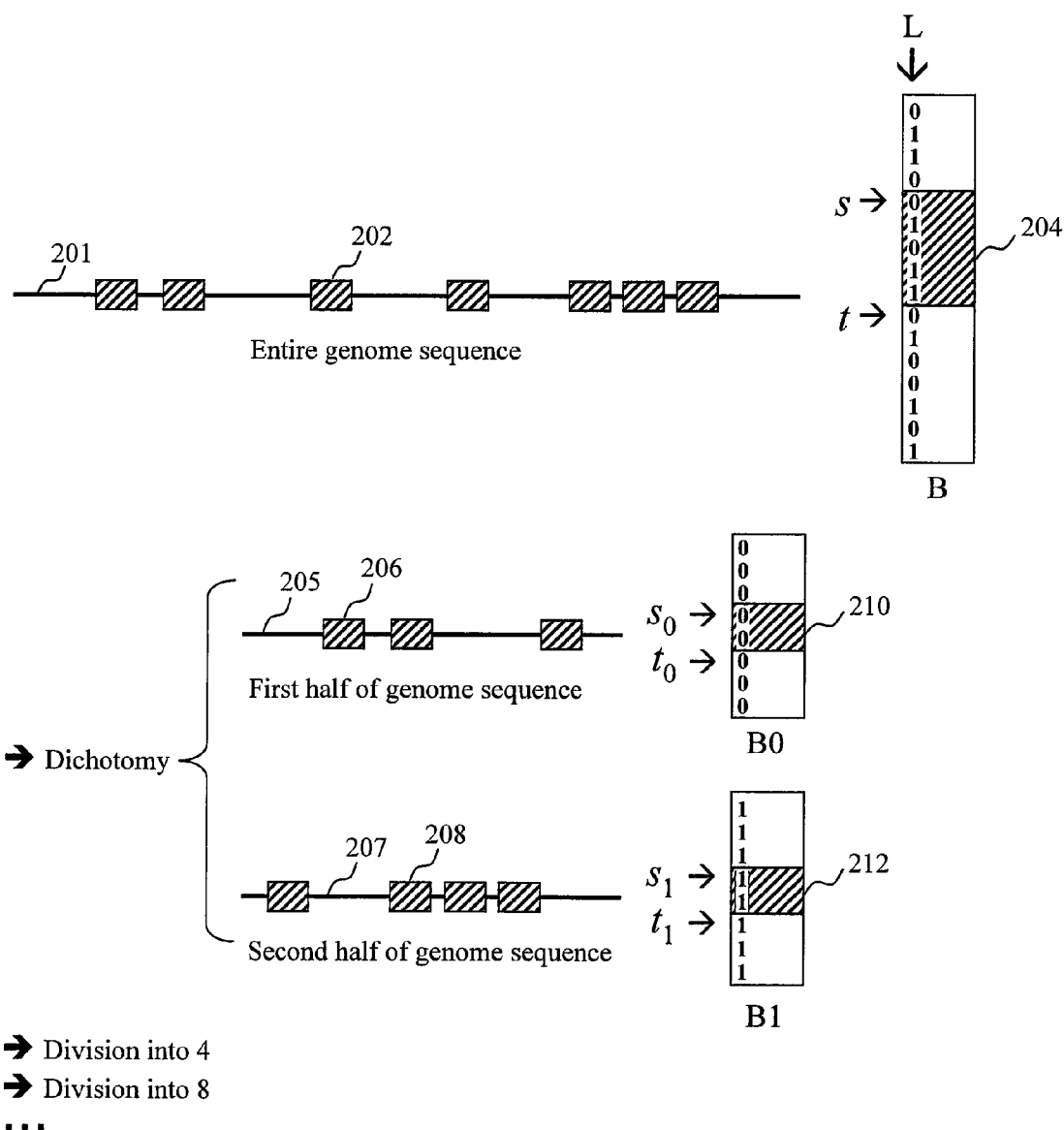
FIG. 2 is a diagram for illustrating a method of dividing index information along with division of a region.

FIG. 2 is a diagram for illustrating a method of dividing the index information when a region is divided. As will be described later, this method is used for configuring the index range localization processor 110. Here, for the sake of simplicity of description, it is assumed that the genome length is a power of two (h-th power of two) minus one. Expansion to a general case of another genome length can be made by easy analogy. It is provided that, as denoted by reference numeral 202, a multiplicity of sequences identical to the query sequence occur on a genome sequence, which is denoted by reference numeral 201, in a scattered manner. In this case, on a suffix array B (203) for a region of the entire genome sequence, according to characteristics of the suffix array, indices corresponding to the multiplicity of scattered occurring positions appear to be assembled in one place as denoted by reference numeral 204. Since it is assumed that the genome length is h-th power of two minus one, the positions of suffixes are represented by respective integers at least zero and less than an h-th power of two. It is provided that a null character string is a final suffix. The index of the suffix corresponding to the first half of the genome is represented by an integer whose most significant bit (h-th bit from the least significant bit) is zero in binary representation. The index of the suffix corresponding to the second half of the genome is represented by an integer whose most significant bit (h-th bit from the least significant bit) is one in binary representation. Thus, by dividing the suffix array B corresponding to the entire genome region according to whether the most significant bit is zero or one while maintaining the internal, relative order, a subarray B0 of the suffix array corresponding to the first half of the genome and a subarray B1 of the suffix array corresponding to the second half of the genome are acquired. By dichotomizing the entire genome sequence, a multiplicity of sequences identical to the query sequence occur on the first half of the genome sequence 205 and the second half of the genome sequence 207 in a scattered manner as denoted by reference numerals 206 and 208. However, indices thereof appear in the subarrays B0 and B1 in an assembled manner as denoted by reference numerals 210 and 212.

Provided that, in the suffix array B corresponding to the entire genome region, the first row is referred to as the 0-th row, the first row of the index range 204 corresponding to the query sequence is the s-th row and the row next to the last row is the t-th row. Likewise, in the suffix array B0 corresponding to the region of the first half of the genome, the first row of the index range 210 corresponding to the query sequence is s0-th row, the row next to the last row is t0-th row. Further, in the suffix array B1 corresponding to the region of the second half of the genome, the first row of the index range 212 corresponding to the query sequence is the s1-th row, and the row next to the last row is t1-th row. In the most significant bit column L of the suffix array B corresponding to the entire genome region, the number of zeros before the s-th row is represented by a rank function rank (L, s, 0), and the number of ones before the s-th row is represented by the rank function rank (L, s, 1), as follows;

s0=rank (L, s, 0),
s1=rank (L, s, 1).

The rank function can be computed at high speed by a publicly-known method (Non Patent Literature 5). Likewise, t0=rank (L, t, 0),
t1=rank (L, t, 1).

Accordingly, in dichotomy of the entire genome region by the most significant bit of the index, division of the index region (s, t) corresponding to the query sequence into parts (s0, t0) and (s1, t1) corresponding to the first and second halves of the genome are computed at high speed. One of the divided parts may be null.

Each of the first and second halves of the genome can be dichotomized in an analogous manner by checking whether the value of the second significant bit of the index ((h−1)-th bit from the least significant bit) is zero or one. This thus divides the entire genome into four. Subsequently, divisions into 8 and 16 can be performed. Finally, the division can recursively be repeated until the region length reaches one.

Figure 3:
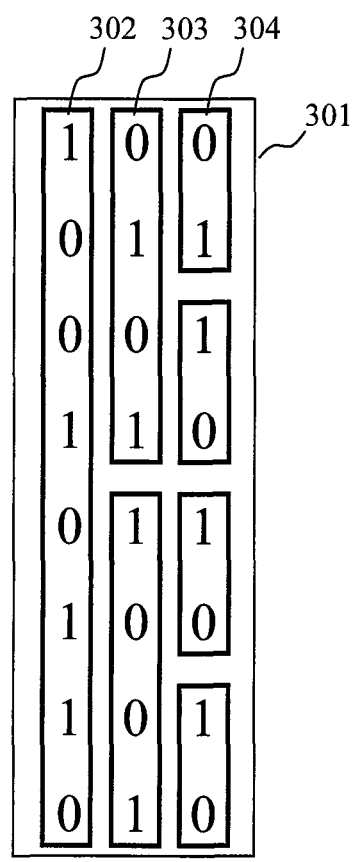
FIG. 3 is a diagram illustrating LSA (localized suffix array).

Such arrangement of bits of the index of the suffix required to compute division of the index range along with the recursive division of the genome region is referred to as LSA (localized suffix array). FIG. 3 is a diagram for illustrating LSA where h=3. Reference numeral 301 denotes the entire LSA. Reference numeral 302 denotes arrangement of the most significant bits of indices in B, which is referred to when the first dichotomy divides the entire genome region into the two regions, or the first and second halves. Reference numeral 303 denotes arrangement of the second significant bits of indices referred to in B0 and B1 in the next division into four, or dichotomy of the two regions. Likewise, reference numeral 304 denotes vertical arrangement of the third significant bits of indices referred to by each region after division into four in the next division into eight. In a case where h>3, also for division into 16 or more, fourth column and thereafter are configured in an analogous manner.

The subregions acquired by the process of recursively dividing the entire genome region as described above are referred to as blocks. The blocks include a block that has an index region corresponding to the query sequence and a block that does not have this index region. The genome positions of the index included in the index range in the block is restricted within the block. The coordinates of the genome positions of the index range are determined while uncertainty corresponding to the block length remains. Accordingly, such a distance (separation) between the index ranges on the genome can be evaluated while the uncertainty remains.

Figure 4:
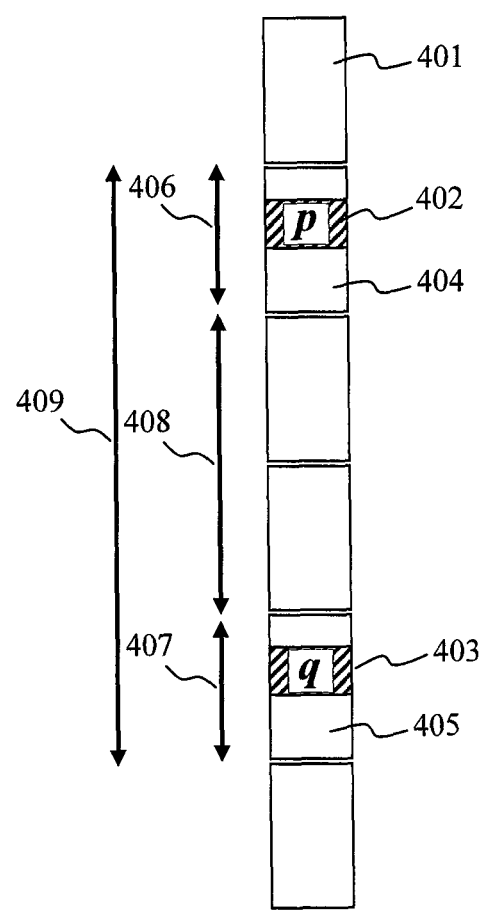
FIG. 4 is a diagram illustrating a method of evaluating a distance between index ranges.

FIG. 4 is a diagram illustrating a method of evaluating a distance on the genome between index ranges included in different blocks in the evaluation processor of the distance between index ranges 117. As will be described later, this evaluation method is used when configuring index range localization processor 110. Reference numeral 401 denotes a block. It is provided that index ranges 402 and 403 for two query sequences p and q are included in different blocks 404 and 405, respectively. The genome positional coordinates of the index ranges are identified while undetermined ranges as denoted by reference numerals 406 and 407 remain. The block length is computed on the basis of the total length of the genome and the number of divisions. Accordingly, the upper limit 409 and the lower limit 408 of the distance between the index ranges can be computed by counting the number of blocks between the blocks 404 and 405.

(lower limit of distance)=(the number of blocks therebetween)×(block length)+1

(upper limit of distance)=((the number of blocks therebetween)+2)×(block length)−1

In a case where the block length becomes one by the last division, these values match with each other. That is, the genome positional coordinates of the index are identified without remaining uncertainty.

Figure 5:
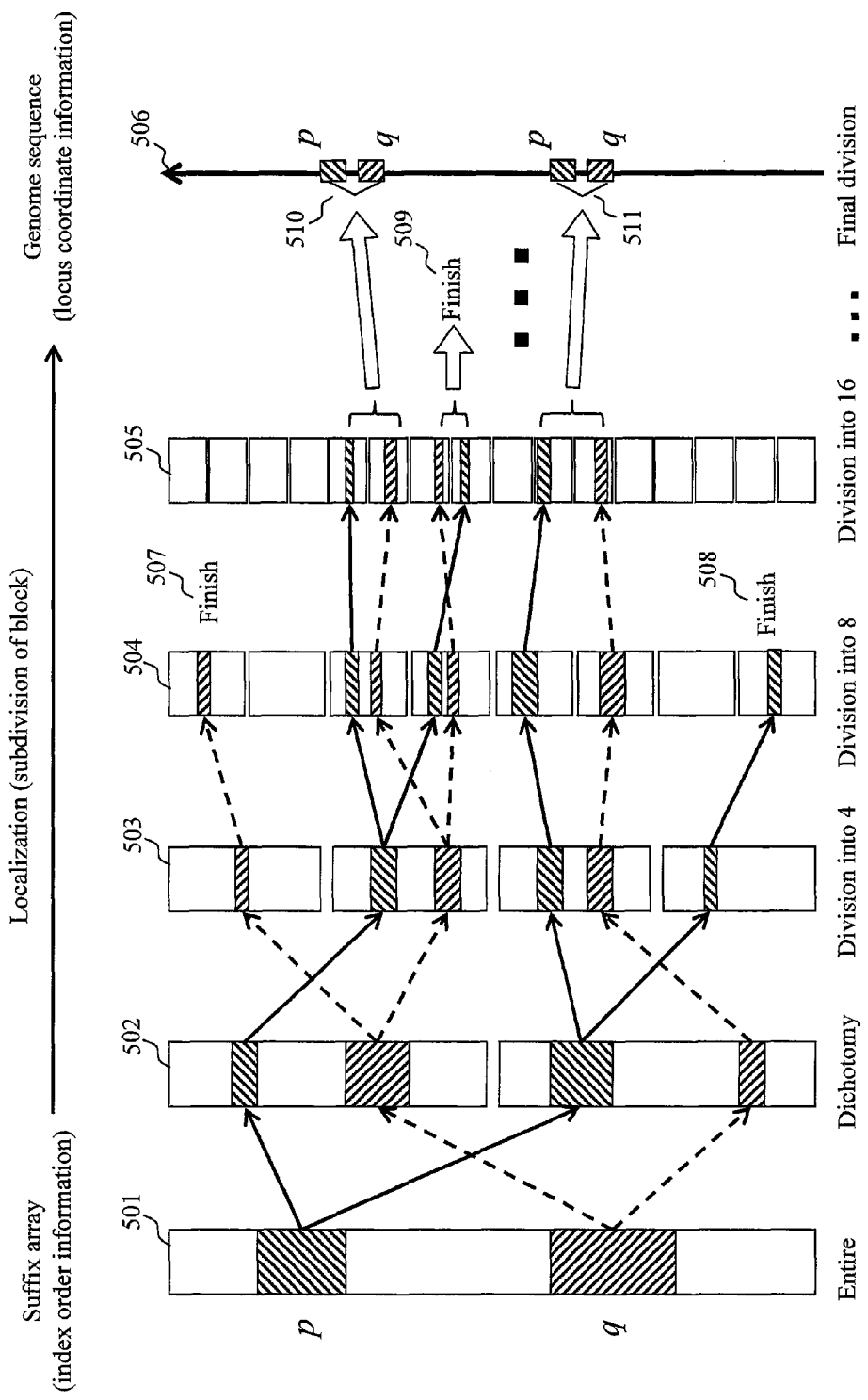
FIG. 5 is a diagram illustrating a process of localizing the index range.

FIG. 5 is a diagram illustrating a manner in which, when index ranges for two query sequences p and q in the entire genome are provided, the index range localization processor 110 recursively repeats division of the genome region and thereby identifies the positional coordinates on the genome sequences as the paired sequences while reducing uncertainty. Reference numeral 501 denotes a suffix array for the entire genome region (initial block). Reference numeral 502 denotes subarrays of suffix arrays corresponding to dichotomized first and second halves/blocks of the entire genome. Reference numeral 503 denotes vertical arrangement of subarrays of suffix arrays corresponding to respective blocks, which are divisions of the entire genome into four. Likewise, reference numerals 504 and 505 denote vertical arrangement of subarrays of suffix arrays corresponding to blocks, which are division of the entire genome into 8 and 16, respectively. Reference numeral 506 denotes a case where the block length finally reaches one. A solid arrow connecting reference numerals 501 to 506 with each other shows a manner in which the index range for the query sequence p is further detailed by a recursive localization process (process of subdividing the block).

Likewise, a broken arrow connecting reference numerals 501 to 506 with each other shows a manner in which the index range for the query sequence q is further detailed by the localization process. In this process, as denoted by reference numerals 507, 508 and 509, the process that does not satisfy a distance constraint between the paired sequences is terminated. What does not satisfy the distance constraint between the paired sequences includes sequences where the order of the paired sequences is inverted as denoted by reference numeral 509. Reference numerals 510 and 511 finally remaining on reference numeral 506 provide mapping positions of the paired sequences.

Figure 6:
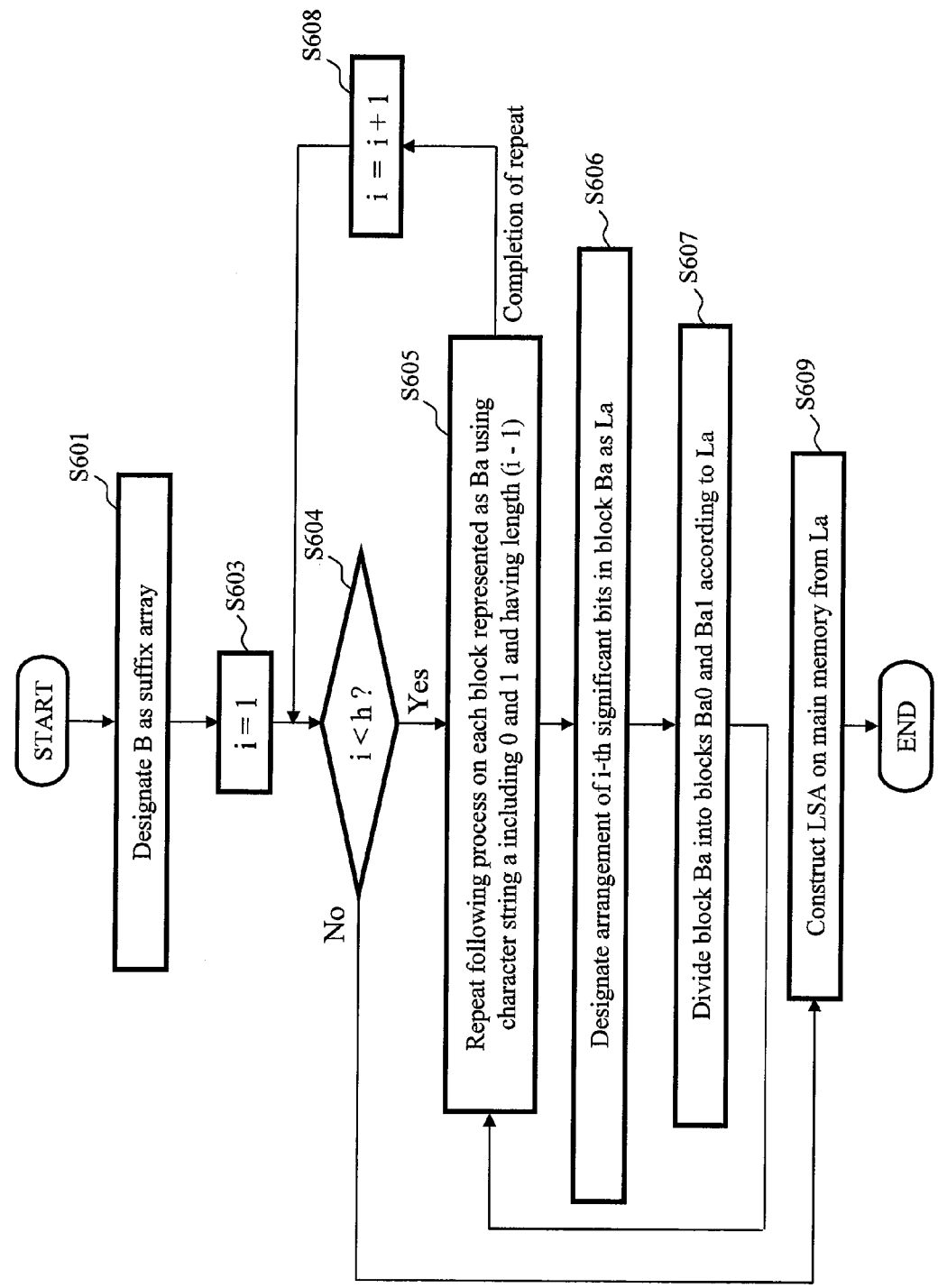
FIG. 6 is a flowchart for illustrating a method of constructing LSA.

FIG. 6 shows a processing procedure of constructing LSA. In step 601, a block B is designated as a suffix array for the entire reference genome sequence computed by the suffix array construction processor 105 and stored in the main memory 104. Analogous to what is described above, for the sake of simplicity of description, it is assumed that the reference genome sequence length is h-th power of two minus one. Reference symbol B denotes an array in which the number, h-th power of two, of indices (h-bit integer) are arranged. In step 603, it is set such that i=1, and the following processing is repeated. Step 604 is a finish determination process. According to step 605, processes in steps 606 and 607 are performed on each block denoted as Ba using a character string "a" including zero and one and having a length (i−1). In step 606, a bit string of arrangement of i-th significant bits of respective indices (h-bit integer) included in the block Ba is denoted as La. In step 607, indices included in Ba are classified into blocks Ba0 A and Ba1 according to whether the bits are zero or one. In this case, the relative order of indices are maintained. After completion of the processing on every Ba, the value of i is incremented by one in step 608 and then the processing is returned to a point immediately before step 604. If the finish condition is satisfied in step 605, LSA is constructed on the main memory 104 from La in step 609.

Figure 7:
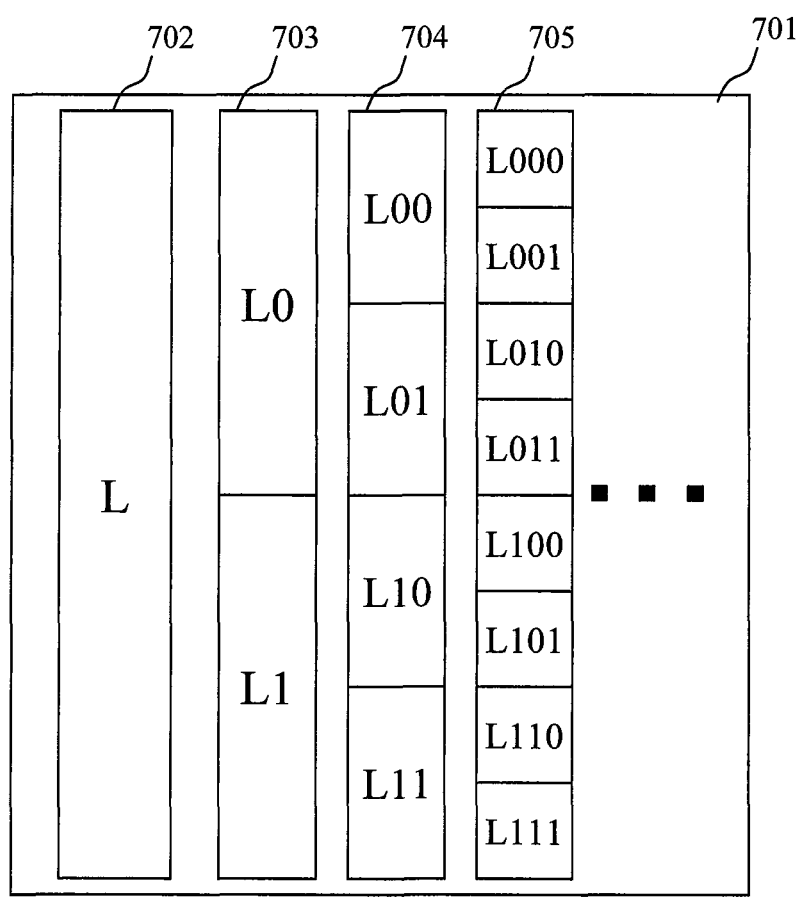
FIG. 7 is a diagram illustrating the method of constructing LSA.

FIG. 7 is a diagram illustrating a method of constructing LSA from La. LSA 701 is arrangement of bits in the number, h-th power of two, of rows and h columns. A first column 702 is equal to L. A second column 703 is a connection of L0 and L1. A third column 704 is a connection of L00, L01, L10 and L11. A fourth column 705 is a connection of L000, L001, L010, L011, L100, L101, L110 and L111. A fifth column and thereafter have analogous configurations.

In actuality, the genome sequence includes characters A, C, G, T and N representing respective nucleotides, and the method according to the present invention is applicable to a character string including general alphabetical characters. FIG. 8 is a diagram illustrating an example of constructing LSA in a case where h=3 and the reference genome sequence is "abracad". Reference numeral 801 denotes a list of all suffixes of "abracad" and respective indices thereof (including a null character string). Reference numeral 802 denotes a list based thereon sorted according to a lexicographic order; this list is a suffix array. Reference numeral 803 denotes a list in which index values of the suffix array are represented in binary representation, and is B corresponding to the entire genome. Reference numeral 804 is LSA constructed from B by the method illustrated in FIG. 6 and corresponds to FIG. 7.

Figure 9:
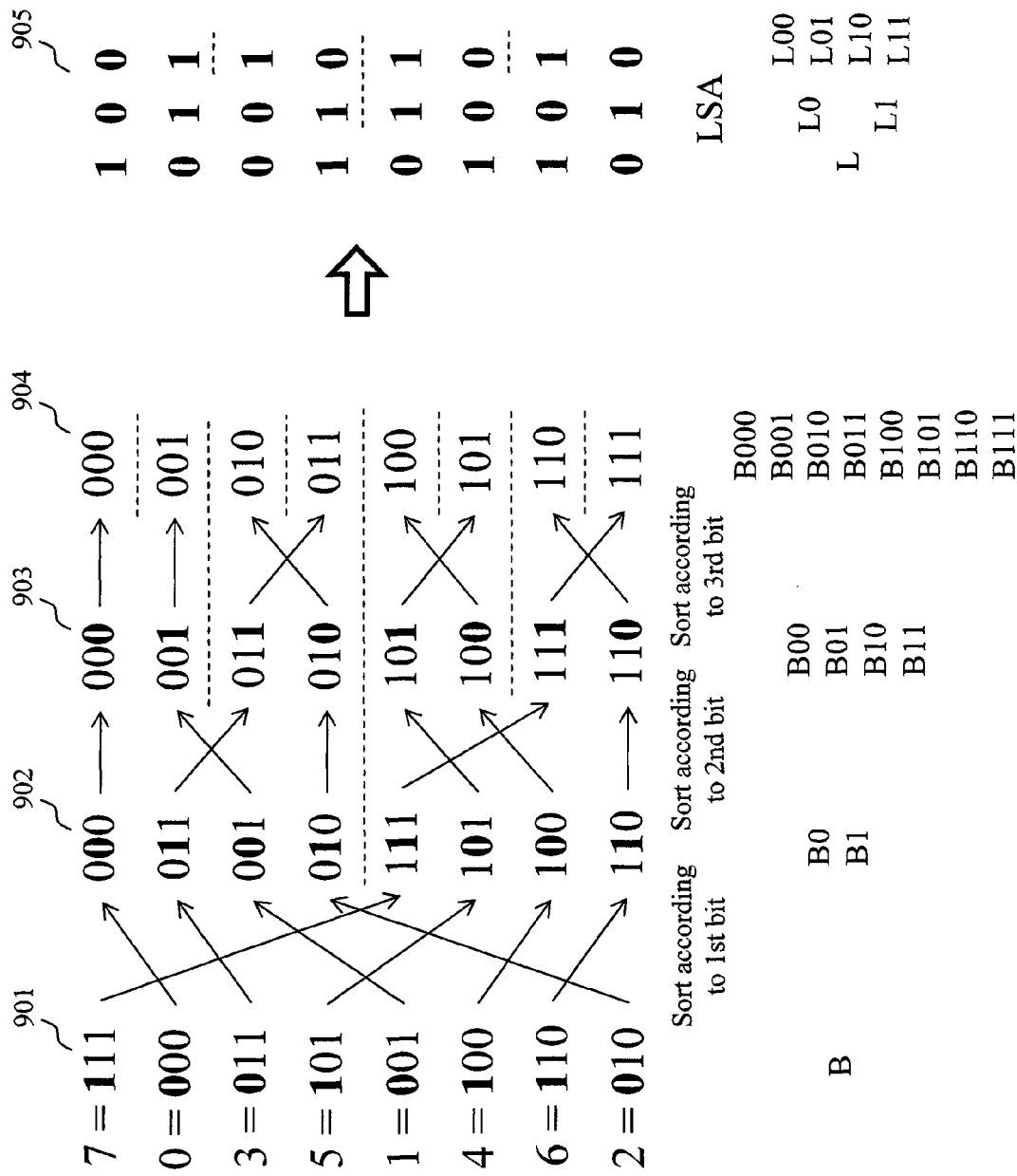
FIG. 9 is a diagram for illustrating a specific example of constructing LSA in detail in a bit-level.

FIG. 9 is a diagram for illustrating a process of constructing LSA from B corresponding to the entire genome according to the method illustrated in FIG. 6 in a case where the reference genome sequence is "abracad". Reference numeral 901 denotes B corresponding to the entire genome. Reference numeral 902 denotes B0 and B1 corresponding to the first and second halves of the genome which are delimited by broken lines and arranged. In division of B into B0 and B1, the most significant bit (boldface) of B is referred to. Arrangement of these bits is L0, which is the first column of LSA denoted by reference numeral 905. Likewise, reference numeral 903 is arrangement of reference numerals B00, B01, B10 and B11, which correspond to division of the genome into four and are delimited by broken lines. In the division of B0 and B1 into B00, B01, B10 and B11, the second significant bits (boldface) of B0 and B1 are referred to. Arrangements of these bits are L0 and L1, which are second columns of LSA denoted by reference numeral 905. Likewise, reference numeral 904 is arrangement of reference numerals B000, B001, B010, B011, B100, B101, B110 and B111, which correspond to division of the genome into eight and delimited by broken lines. In the division of B00, B01, B10 and B11 into these eight, third significant bits (boldface) of B00, B01, B10 and B11 are referred to. Arrangements of these bits are reference numerals L00, L01, L10 and L11, which are third columns of LSA denoted by reference numeral 905. In 904, the block length is one, where recursive division is finished. Accordingly a bit matrix with eight rows and three columns denoted by reference numeral 905 is LSA.

Figure 10:
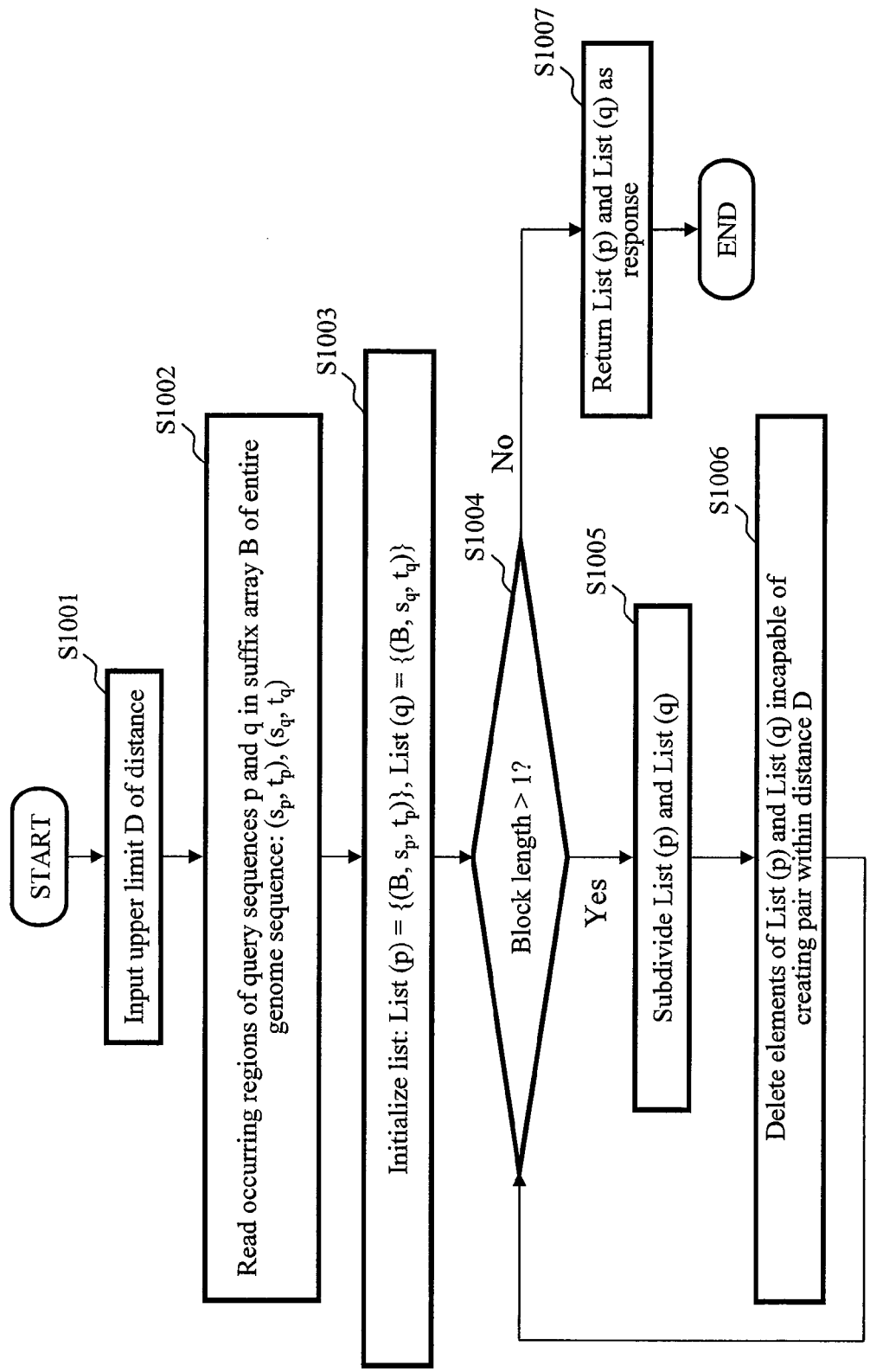
FIG. 10 is a flowchart illustrating processing procedures of a process of localizing the index range.

FIG. 10 is a diagram is a diagram illustrating a processing flow in the index range localization process 110. In step 1001, the upper limit value D of the distance is read from the user via the input device 106. In step 1002, an occurring region $(s_p, t_p)$ of the query sequence p and an occurring region $(s_q, t_q)$ of the query sequence q in the suffix array B of the entire genome sequence are read from the main memory 104. B has already been constructed by the suffix array construction processor 105, values of $(s_p, t_p)$ and $(s_q, t_q)$ have already been computed by the index range retrieval processor 109; these values are held in the main memory 104. In step 1003, information List (p) representing a list of candidates of mapping positions of the query sequence p and information List (q) representing a list of candidates of mapping positions of the query sequence q are initialized as represented in the respective following expressions.

$$\text{List }(p)=\{(B, s_p, t_p)\},$$

$$\text{List }(q)=\{(B, s_q, t_q)\}.$$

These lists are updated in order to identify the coordinates of the mapping positions in detail by the following repetitive processing. Step 1004 is a finish determination process of this repetitive process. If the block length becomes one, it is determined to be finished. In step 1005, the list List (p) is updated by subdividing each element belonging to the list List (p) with reference to FIG. 11 according to a method described below. Likewise, the list List (q) is updated by subdividing each element belonging to the List (q).

As described with reference to FIG. 4, the mapping positions of the index range of each query sequence are identified while a block length of uncertainty remains. Based thereon, the upper and lower limits of the distance between the mapping positions of the index ranges belonging to different blocks can be evaluated. In step 1006, the elements of the lists List (p) and List (q) are evaluated in a combined manner, and the elements of the lists List (p) and List (q) incapable of creating a pair having the upper limit of the distance between the pair within D is deleted. In a case of considering the combination of elements in the lists List (p) and List (q), it is effective to preliminarily sort the elements in the order of the mapping positions. After completion of the repetitive processing, the lists List (p) and List (q) are returned to the main memory 104 as a response in step 1007.

Figure 11:
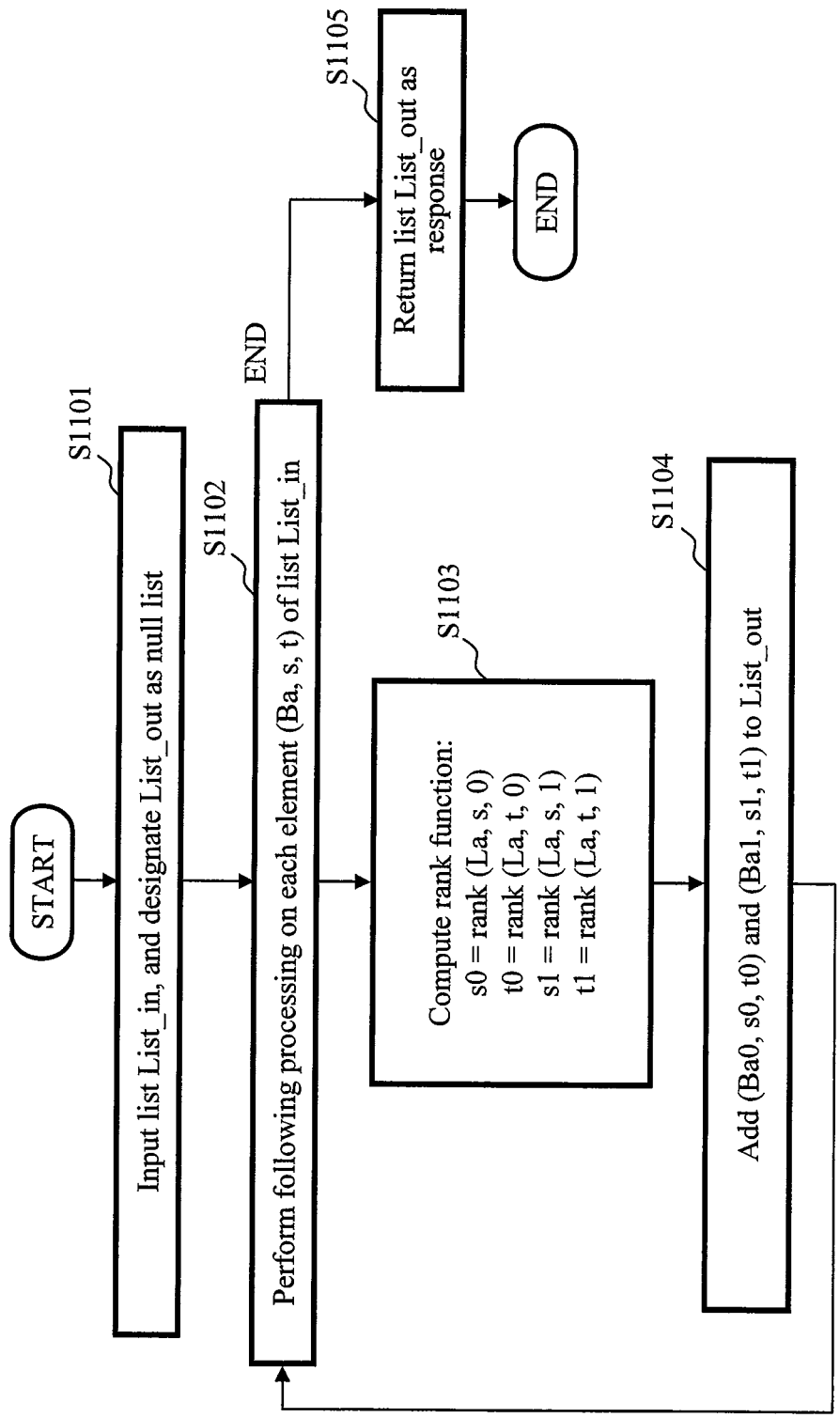
FIG. 11 is a flowchart illustrating a method of updating a list of the index range.

FIG. 11 is a flowchart illustrating a processing procedure of a process 1005 of subdividing the list that updates information List_in representing a candidate list of the mapping positions of the query sequence and returns the new list List_out as a response. This processing procedure is a method analogous to that illustrated with reference to FIG. 2. In step 1101, the list List_in is input, and the list List_out is set to a null list. The List_in is List (p) or List (q) before the subdivision in step 1005. In step 1102, the following processing is performed on each element (Ba, s, t) of the list List_in. Here, "a" represents a character string including zero and one. "s" and "t" are integers representing the index range of the query sequence in the block Ba. In step 1103, according to the following expressions, integers s0, t0, s1 and t1, which represent the index ranges in the subdivided blocks Ba0 and Ba1, are computed.

s0=rank (La, s, 0),
t0=rank (La, t, 0),
s1=rank (La, s, 1), and
t1=rank (La, t, 1), where rank (La, s, 0) is a rank function and represents the number of zeros appearing before the position of s-th row in the bit string La in LSA; rank (La, s, 1) is also a rank function and represents the number of ones appearing before the position of the s-th row in the bit string La in LSA. The rank function can efficiently be computed by a publicly-known method (Non Patent Literature 5). This is also applicable to rank (La, t, 0) and rank (La, t, 1). In step 1104, (Ba, s, t) is divided into two blocks (Ba0, s0, t0) and (Ba1, s1, t1) according to whether each corresponding bit in the bit string La in LSA is zero or one, and these blocks are added to the list List_out. In step 1105, the acquired list List_out is returned to the main memory 104 as a response. This becomes List (p) or List (q) after subdivision in step 1005.

The present invention compactly represents a multiplicity of mapping position candidates for the query sequence as the index ranges (two integers s and t) in the blocks. The mapping positions of the index range can be identified in detail to a nucleotide level, while reducing the undetermined range, by repeating the subdivision of the block and accompanying division of the index range. In this case, the upper limit of the distance between the mapping positions where the undetermined range remains is evaluated, and index information for the mapping positions incapable of satisfying the interval constraint (within the distance D) of the mapping positions designated between the pair is removed, thereby avoiding useless computation. The division of the index range along with the division of the block can efficiently be computed by referring to LSA. The processing procedure for efficiently constructing LSA is also provided.

As described above, in a case where large-scale reference genome sequence data and massive paired-end sequence data (query sequence data) are provided, a combination of mapping positions of the paired sequences that has a separation of the mapping positions between the pair within a preliminarily designated value can be acquired at high speed.

Embodiment 2

The above embodiment describes the computation method of genome mapping of the query sequence acquired by the paired-end method. The present invention is also applicable to a problem of genome mapping computation of the query sequence acquired by sequencing fragment sequences of a cDNA sequence created from spliced mRNA.

Figure 12:
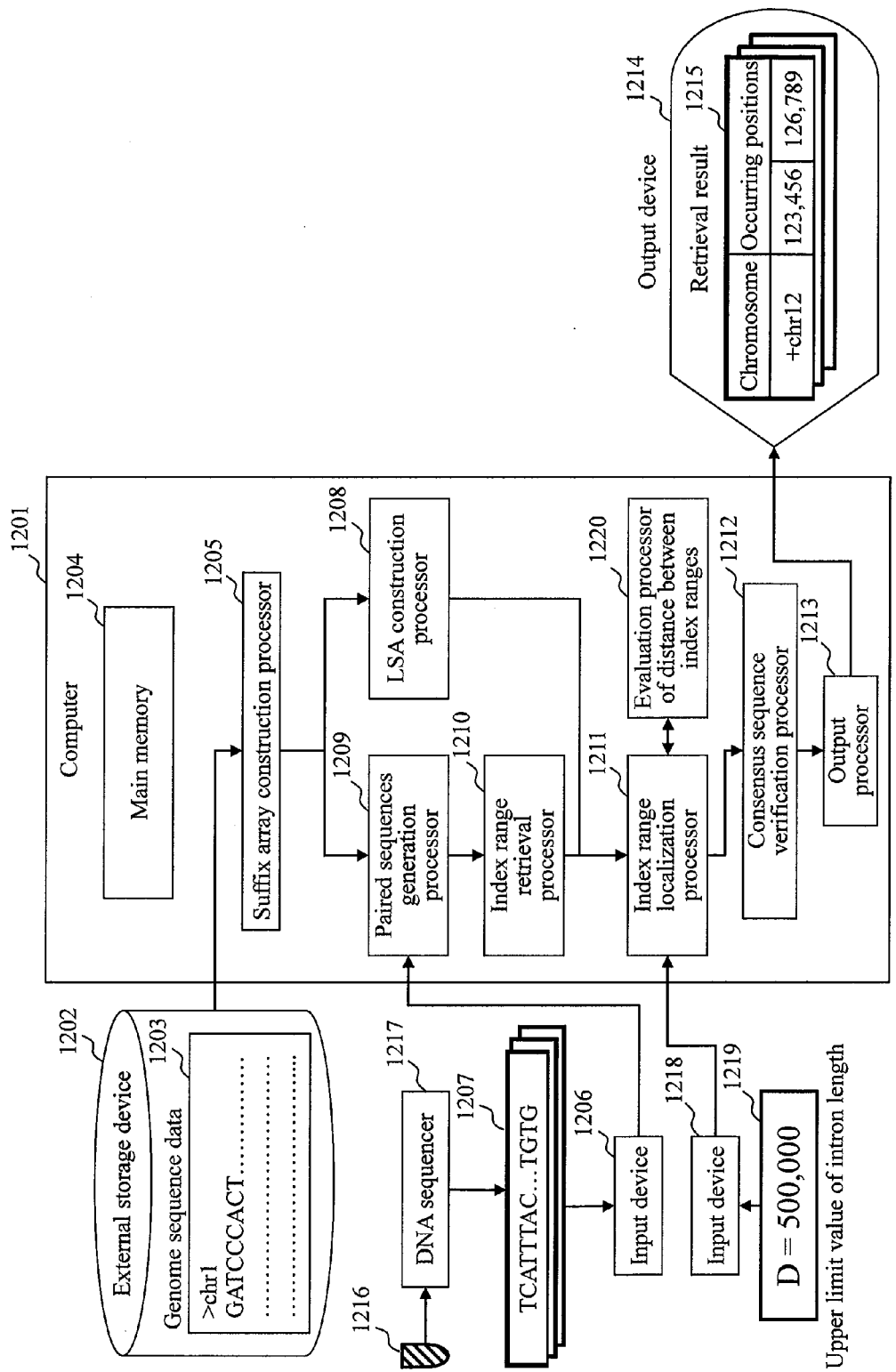
FIG. 12 is a diagram showing an example of a configuration of a system that performs genome mapping computation including splicing.

FIG. 12 is a diagram showing an example of a configuration of a system that performs genome mapping computation including splicing according to the embodiment. Reference numeral 1201 denotes a computer operating this system. This computer reads reference genome sequence data 1203 stored in an external storage device 1202, reads via an input device 1206 query sequence data 1207 acquired by analyzing a cDNA sample 1216 using a DNA sequencer 1217, and reads via an input device 1218 a parameter 1219 (upper limit value D of an intron length) designated by a user. The computer 1201 causes the suffix array construction processor 1205 to connect nucleotide sequences in the reference genome sequence data 1203 via a delimiter $, computes a suffix array thereof and stores the array in the main memory 1204. Likewise, computation results of other processors are stored in the main memory 1204, and the contents of the results are referred to by each processor as necessary.

An LSA construction processor 1208 constructs a new index information LSA (localized suffix array) on the basis of the suffix array. A paired sequences generation processor 1209 dichotomizes the query sequence at various positions, thereby creating various paired sequences. An index range retrieval processor 1210 searches the suffix array with respect to each of paired sequences in an independent manner, and acquires index information. An index range localization processor 1211 determines the coordinates corresponding to the index satisfying a constraint that the mapping position separation between the pair does not exceed the upper limit value of the intron length on the basis of the index information of the paired sequences and LSA of the reference genome sequence, while gradually localizing the coordinates from the entire genome. This allows the mapping positions for the paired sequences to be acquired.

A consensus sequence verification processor 1212 verifies the genome sequence at and around a splicing site, and removes a mapping result that does not satisfy a consensus.

An output processor 1213 outputs mapping position information (retrieval result 1215) to an output device 1214. The mapping information (retrieval result 1215) of the spliced sequence includes information of the chromosome name, the direction (which one of + and − strands), and coordinates representing two spliced occurring positions.

The processing details of the suffix array construction processor 1205, the LSA construction processor 1208, the index range retrieval processor 1210, the index range localization processor 1211 and the like are analogous to those in Embodiment 1. The paired sequences generation processor 1209 preliminarily designates a lower limit value of the length of the paired sequences acquired by division, and generates all paired sequences satisfying the condition. These are processed as paired sequences data by the index range retrieval processor 1210 and the index range localization processor 1211, and further analyzed as spliced mapping and verified by the consensus sequence verification processor 1212. As to the consensus of the genome sequence at and around the splice site, a part sandwiched by the genome/mapping positions as the paired sequences are analyzed as intron sequences, and a condition that the intron sequence starts at GT and ends at AG is imposed. Mapping results of the paired sequences that do not satisfy this condition is removed.

In a case where a large-scale reference genome sequence data and massive query sequence data acquired by sequencing cDNA are provided, the method of acquiring a combination of the mapping positions of the paired sequences where the separation of the mapping positions between the pair is within a preliminarily designated value at high speed as described in the above embodiment is thus used as described above. Accordingly, genome mapping including splicing of an appropriate length of an intron sequence (e.g. within hundreds of thousands of nucleotides) can be computed at high speed.

Embodiment 3

In the above embodiment, the embodiment for nucleotide sequence data including A, C, G, T and N has been described. The present invention is also applicable to general character string data, which is not limited to nucleotide sequence data. Here, an embodiment on amino acid fragment sequence data is described. The amino acid sequence is a sequence including approximately 20 types of amino acids.

Figure 13:
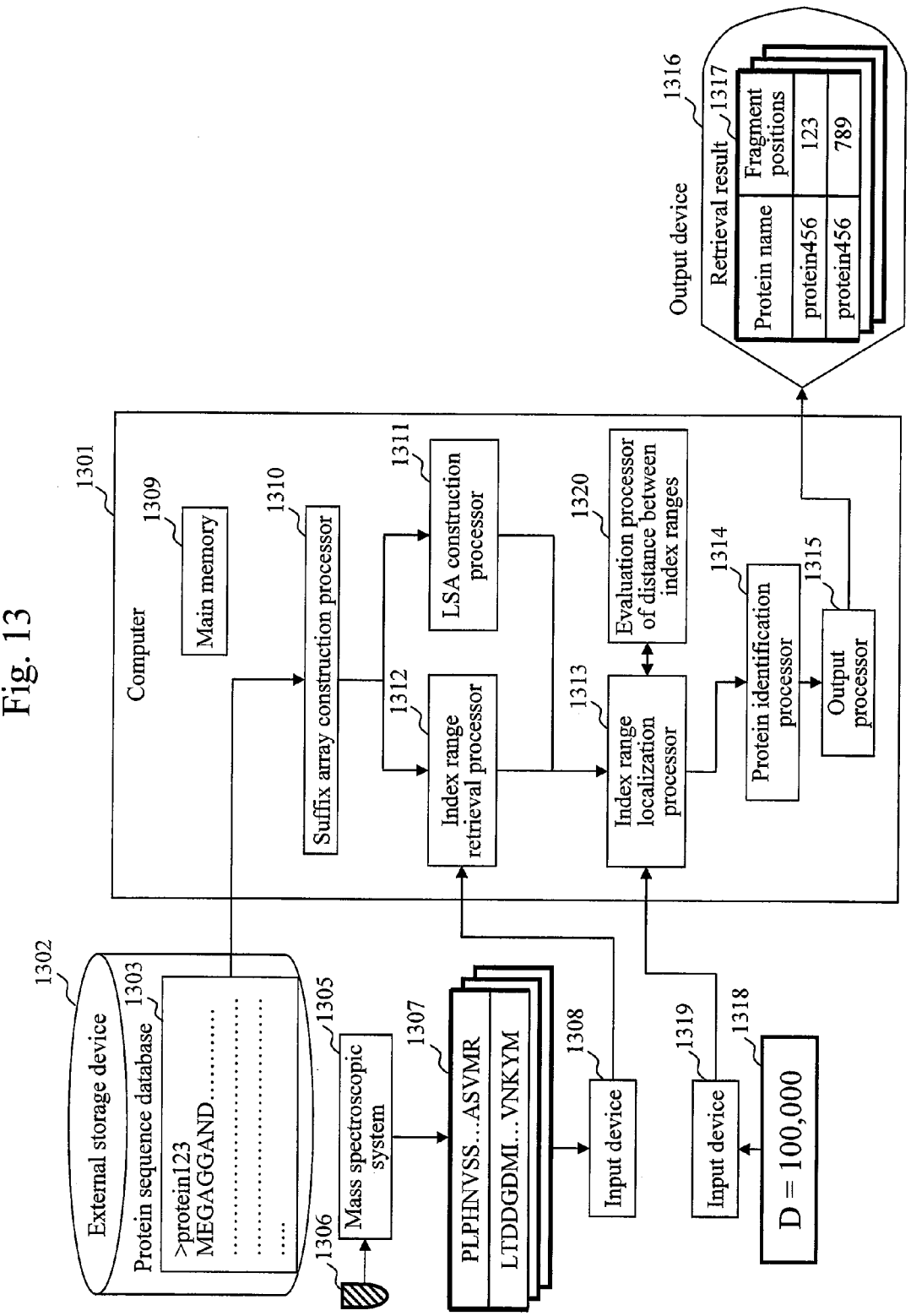
FIG. 13 is a diagram showing an example of a configuration of a system that identifies a protein from an amino acid sequence fragment.

FIG. 13 is a diagram showing an example of a configuration of a system that identifies a protein from amino acid fragment sequence according to the embodiment. Reference numeral 1301 denotes a computer operating this system. This computer reads reference protein sequence data 1303 stored in an external storage device 1302, reads via an input device 1308 plural pieces of query sequence data 1307 acquired by analyzing a protein sample 1306 using a mass spectroscopic system 1305, and reads via an input device 1319 a parameter 1318 (upper limit value D of the protein sequence length) designated by a user. The computer 1301 causes a suffix array construction processor 1310 to connect amino acid sequences in the reference protein sequence data 1303 to each other via a delimiter $, computes a suffix array thereof, and stores them in a main memory 1309. Likewise, computation results of other processors are also stored in the main memory 1309, the contents thereof are referred to by each processor as necessary.

An LSA construction processor 1311 constructs index information LSA (localized suffix array) on the basis of the suffix array. An index range retrieval processor 1312 searches the suffix array with respect to each query sequence in an independent manner, and acquires index information. An index range localization processor 1313 determines occurring positions of the index that appear in close proximity to each other in the reference protein sequence data 1303 on the basis of the index information of the query sequence and LSA of the reference genome sequence while gradually localizing the occurring positions from the entire reference protein sequence data. This allows occurring positions in the reference protein sequence data as a group of query sequences to be acquired. A protein identification processor 1314 identifies a protein including the query sequence on the basis of the occurring positions of query sequence in the reference protein sequence data, and identifies a protein including a plurality of query sequences. An output processor 1315 outputs a retrieval result 1317 including information the name of the identified protein and occurring positions (fragment positions) of the query sequence to an output device 1316.

Processing details of the suffix array construction processor 1310, the LSA construction processor 1311, the index range retrieval processor 1312, the index range localization processor 1313 and the like are analogous to those in the above embodiment.

In a case where large-scale reference protein sequence data and massive query sequence data (amino acid sequence data) acquired by analyzing a protein sample using the mass spectroscopic system are provided, the method of acquiring a combination of the mapping positions of the paired sequences where the separation of the mapping positions between the pair is within the preliminarily designated value at high speed as described in the above embodiment is thus used as described above. Accordingly, the occurring positions of the query sequence in the reference protein sequence data that appear in close proximity of each other can be acquired. This in turn enables a protein including a plurality of occurring positions of the query sequence to be identified at high speed in a highly reliable manner.

Embodiment 4

The above embodiments have dealt with biological sequence data, such as the nucleotide sequence and the amino acid sequence. However, the present invention is also applicable to general document data.

Figure 14:
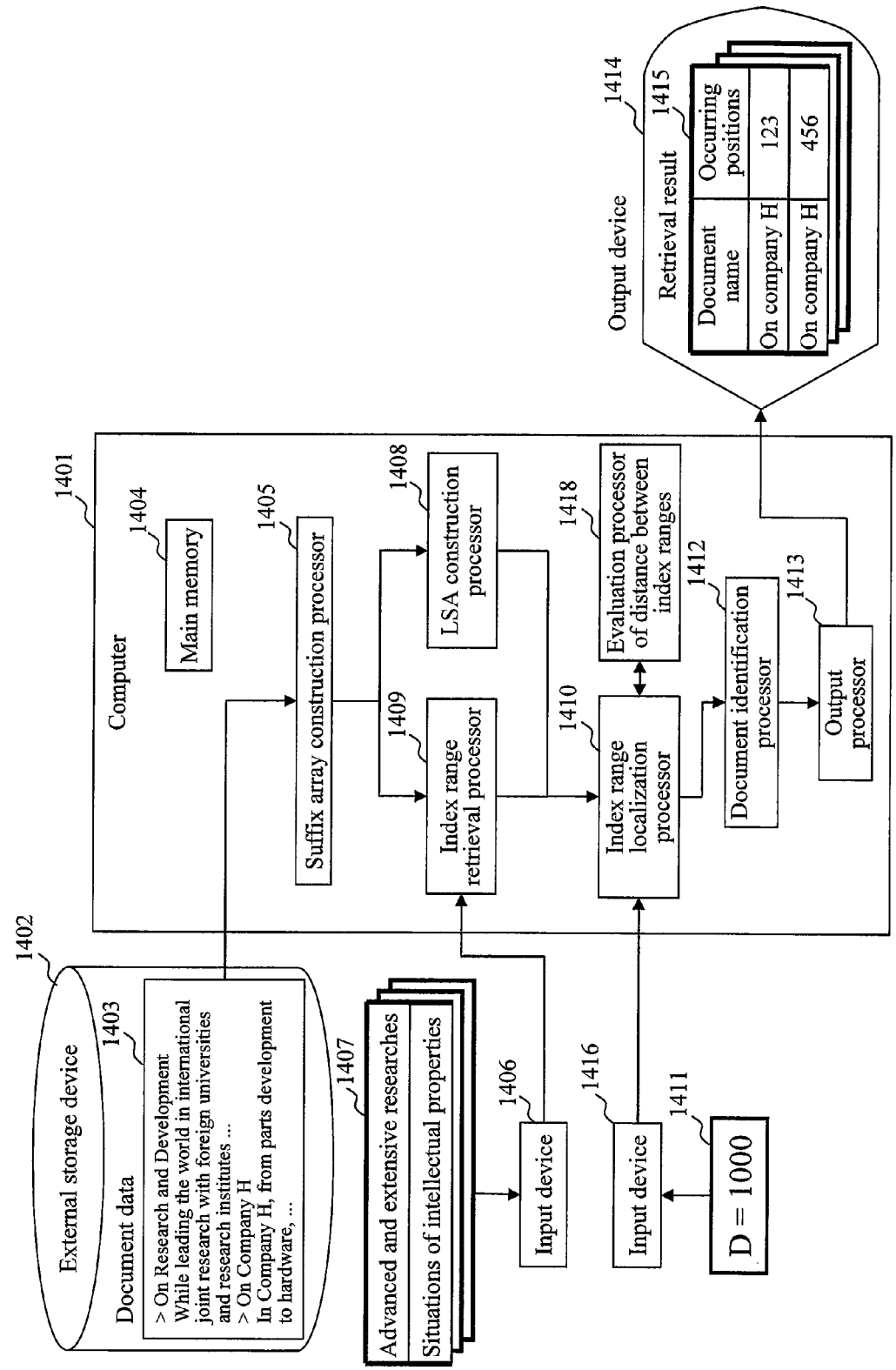
FIG. 14 is a diagram showing an example of a configuration of a system that performs computation identifying a document in which two character strings appear in close proximity to each other from general document data.

FIG. 14 is a diagram showing an example of a configuration of a system that performs computation identifying a document in which two retrieval character strings appear in close proximity to each other from general document data of this embodiment. Reference numeral 1401 is a computer operating this system. This computer reads reference document data 1403 stored in an external storage device 1402, reads a pair of retrieval character strings (query) 1407 via an input device 1406, and reads via an input device 1416 parameter 1411 (an upper limit value D of the distance between the pair) designated by a user. This embodiment assumes that the reference document data 1403 is a group of documents including text of the character string accompanied by its text name. However, the present invention is also applicable to a general structured document having a hierarchical structure by an easy analogy.

The computer 1401 causes a suffix array construction processor 1405 to connect character strings in the document data 1403 via a distinguishable delimiter, compute a suffix array thereof, and stores them in a main memory 1404. Likewise, computation results of other processors are also stored in the main memory 1404, the contents thereof are referred to by each processor as necessary. An LSA construction processor 1408 constructs index information LSA (localized suffix array) on the basis of a suffix array. An index range retrieval processor 1409 searches the suffix array with respect to each retrieval character string in an independent manner, and acquires index information. An index range localization processor 1410 determines occurring positions for the index in the document that appear in close proximity to each other in the document data 1403 on the basis of the index information of the retrieval character string and LSA of the document data while gradually localizing the positions from the entire document. This allows the occurring positions in the document to be acquired as a pair of retrieval character strings. A document identification processor 1412 verifies whether two retrieval character strings occur in the same document in the document data or not. An output processor 1413 outputs, to an output device 1414, a retrieval result 1415 including information of the document names of the documents where two retrieval character strings occur in close proximity to each other and respective occurring positions of the retrieval character strings.

Processing details of the suffix array construction processor 1405, the LSA construction processor 1408, the index range searching section 1409, the index range localization processor 1410 and the like are identical to those in the above embodiment.

In a case where the large-scale document data and the massive retrieval character string pair are provided, the method of acquiring at high speed a combination of the occurring positions of the pair of character strings where the separation of the occurring positions between the pair is within the preliminarily designated value as described in the above embodiment is thus used as described above. Accordingly, the occurring positions of the retrieval character string in the document data appearing in close proximity to each other can be acquired. The document in which these occur can be identified at high speed.

REFERENCE SIGNS LIST

201 Reference genome sequence
202 Positions where sequence identical to query sequence occur on reference genome sequence
204 Index range corresponding to query sequence in suffix array for entire reference genome
205 First half of reference genome
206 Positions where sequence identical to query sequence occurs on first half of reference genome
207 Sequence of second half of reference genome
208 Positions where sequence identical to query sequence occurs on sequence of second half of reference genome
210 Index range corresponding to query sequence in suffix array for first half of reference genome
212 Index range corresponding to query sequence in suffix array for second half of reference genome

The invention claimed is:

1. A pair character string retrieval system, comprising:
a storing device storing a reference character string;
an input device inputting paired first and second character strings, and an upper limit value of a distance between the first and second character strings;
a suffix array construction processor constructing a suffix array of the reference character string;
an index range retrieval processor computing an index range in the suffix array for each of the first and second character strings in an independent manner;
an LSA construction processor that designates the suffix array as an initial block, divides the suffix array into two blocks corresponding to subregions that are first and second halves of the reference character string according to most significant bits thereof being zero or one, designates arrangement of the most significant bits, having been referred to, as a first column of LSA, further dichotomizes the acquired two blocks according to whether second significant bits are zero or one, thus dividing these two blocks into four blocks corresponding to subregions dividing the entire reference character string such as the entire reference genome sequence into four, designates arrangement of the second significant bits, having been referred to, as a second column of LSA, repeats analogous processing until the length of the subregion becomes one, computes each column of LSA in the processing, and thereby constructs localizable index information LSA;

an index range localization processor that designates the respective index ranges in the suffix array that correspond to the first and second character strings as index ranges in the initial block, divides the index range in the initial block into the index ranges in the blocks using information of the first column of the LSA according to division into the two blocks corresponding to the subregions that are the first and second halves of the reference character string, divides the index ranges in the two blocks into index ranges in the four blocks using information of the second column of the LSA according to division into the four blocks corresponding to the subregions dividing the entire reference character string into four, repeats analogous processing thereafter, and performs computation of localizing the index range in the initial block into the index range in the subregion in the reference character string;

an evaluation processor of the distance between index ranges that evaluates an upper limit of a distance between the first and second character strings localized into the subregions in the reference character string such that positional coordinates of the index ranges localized into the subregions on the reference character string have a remaining undetermined range corresponding to the subregions; and an output device outputting positions on the reference character string of the first and second character strings paired in a distance not exceeding the upper limit value, wherein the index range localization processor removes information of the index range incapable of creating a pair in a distance not exceeding the upper limit value, as a result of information of the index range which becomes null in the computation process and evaluation by the evaluation processor of the distance between index ranges.

2. The pair character string retrieval system according to claim 1, wherein the index range localization processor applies a rank function to the block of each column of the LSA, and computes the positions of the index ranges in the two blocks that are divisions of the block concerned.

3. The pair character string retrieval system according to claim 1,
wherein the reference character string is reference genome sequence data, and
the paired first and second character strings are first and second nucleotide sequences of DNA acquired by a DNA sequencer.

4. The pair character string retrieval system according to claim 1,
wherein the reference character string is reference genome sequence data,
the paired first and second character strings are a pair of first and second nucleotide sequences generated by dichotomizing a nucleotide sequence of cDNA acquired by a DNA sequencer, and
the upper limit value is an upper limit value of an intron length,
the system further comprising a consensus verification processor that verifies a consensus sequence at and around a splice site in the reference genome sequence data, and
the consensus verification processor analyzes a part sandwiched by the first and second nucleotide sequences as an intron sequence, and removes a retrieval result in which a consensus sequence does not appear at or around the splice site.

5. The pair character string retrieval system according to claim 1, further comprising:
a protein identification processor,
wherein the reference character string is a plurality of pieces of reference protein sequence data,
the paired first and second character strings are two amino acid sequences of a fragmented protein acquired by a mass spectroscopic system,
the suffix array construction processor connects amino acid sequences in the plurality of pieces of reference protein sequence data to each other via a delimiter, and computes a suffix array thereof,
the protein identification processor identifies a protein including the paired two amino acid sequences, and
the output device outputs a name of the identified protein, and information of occurring positions of the paired two amino acid sequences.

6. The pair character string retrieval system according to claim 1, further comprising:
a document identification processor,
wherein the reference character string is reference document data in which a plurality of pieces of document data are connected via a distinguishable delimiter,
the document identification processor verifies whether the paired first and second character strings occur in an identical document or not, and
the output device outputs a name of the document including the paired first and second character strings and information of occurring positions of the first and second character strings.

* * * * *